US011229513B2

(12) United States Patent
Sengun (10) Patent No.: US 11,229,513 B2
(45) Date of Patent: Jan. 25, 2022

(54) WHIP-STITCHING WITH REINFORCEMENT MATERIAL

(71) Applicant: DePuy Mitek, LLC, Raynham, MA (US)

(72) Inventor: Mehmet Z. Sengun, Canton, MA (US)

(73) Assignee: Medos International Sarl, Le Locle (CH)

( * ) Notice: Subject to any disclaimer, the term of this patent is extended or adjusted under 35 U.S.C. 154(b) by 113 days.

(21) Appl. No.: 16/233,495

(22) Filed: Dec. 27, 2018

(65) Prior Publication Data

US 2019/0125518 A1    May 2, 2019

Related U.S. Application Data

(62) Division of application No. 14/579,537, filed on Dec. 22, 2014, now Pat. No. 10,182,903.

(51) Int. Cl.
*A61F 2/08*        (2006.01)

(52) U.S. Cl.
CPC .......... *A61F 2/08* (2013.01); *A61F 2002/087* (2013.01); *A61F 2220/0075* (2013.01); *A61F 2240/001* (2013.01); *A61F 2250/0018* (2013.01)

(58) Field of Classification Search
CPC ........ A61B 17/0401; A61B 2017/0414; A61B 2017/0417; A61B 2017/0404; A61F 2/0811; A61F 2220/0075; A61F 2002/0852; A61F 2002/087; A61F 2002/0882; A61F 2/08
See application file for complete search history.

(56) References Cited

U.S. PATENT DOCUMENTS

| | | |
|---|---|---|
| 5,306,301 A | 4/1994 | Graf et al. |
| 5,645,588 A | 7/1997 | Graf et al. |
| 8,202,318 B2 | 6/2012 | Willobee |
| 8,298,247 B2 | 10/2012 | Sterrett et al. |
| 8,298,281 B2 | 10/2012 | Majercak et al. |
| 8,460,350 B2 | 6/2013 | Albertorio et al. |
| 8,591,544 B2 | 11/2013 | Jolly et al. |
| 8,591,578 B2 | 11/2013 | Albertorio et al. |
| 8,663,324 B2 | 3/2014 | Schmieding et al. |
| 10,182,903 B2 | 1/2019 | Sengun |
| 2007/0239275 A1 | 10/2007 | Willobee |
| 2007/0250163 A1 | 10/2007 | Cassani |

(Continued)

FOREIGN PATENT DOCUMENTS

EP        1530976 A1 *  5/2005  ............. A61L 17/14

*Primary Examiner* — Brian A Dukert
*Assistant Examiner* — Rebecca Lynee Zimmerman (57) ABSTRACT

Systems and methods for preparing a ligament graft construct for a ligament reconstruction or repair procedure are provided. In general, the described techniques utilize a reinforcement material having at least one suture tail extending therefrom. The reinforcement material is a ribbon or a ribbon-like flattened portion attached to or integrally formed with the at least one suture tail. To prepare a tissue repair construct, the reinforcement material is positioned on a first surface of a graft to extend from an end thereof and the at least one suture tail, coupled to a needle, is repeatedly passed through the reinforcement material and the surface of the graft to a second surface of the graft, and around a side portion of the graft to thereby create multiple suture loops. The tissue repair construct can be formed on each end of the graft.

17 Claims, 7 Drawing Sheets

(56) References Cited

U.S. PATENT DOCUMENTS

| | | |
|---|---|---|
| 2009/0018655 A1 | 1/2009 | Brunelle et al. |
| 2009/0105754 A1 | 4/2009 | Sethi |
| 2010/0249802 A1 | 9/2010 | May et al. |
| 2012/0046746 A1* | 2/2012 | Konicek .................. A61F 2/08 |
| | | 623/13.14 |
| 2012/0059468 A1* | 3/2012 | Mattern ............... A61F 2/0811 |
| | | 623/13.14 |
| 2013/0023907 A1 | 1/2013 | Sterrett et al. |
| 2013/0023927 A1 | 1/2013 | Cassani |
| 2014/0074239 A1 | 3/2014 | Albertorio et al. |
| 2014/0172096 A1* | 6/2014 | Koob ...................... D04C 1/12 |
| | | 623/13.19 |
| 2014/0277448 A1 | 9/2014 | Guerra et al. |
| 2015/0066079 A1* | 3/2015 | Schmieding ..... A61B 17/06166 |
| | | 606/228 |
| 2017/0156727 A1* | 6/2017 | Wilson-Wirth ....... A61L 17/105 |
| 2018/0360440 A1* | 12/2018 | Guerra ................. A61F 2/0811 |

* cited by examiner

WHIP-STITCHING WITH REINFORCEMENT MATERIAL

CROSS REFERENCE TO RELATED APPLICATIONS

The present application is a divisional of U.S. patent application Ser. No. 14/579,537 entitled "Whip-Stitching With Reinforcement Material" filed Dec. 22, 2014, which is hereby incorporated by reference in its entirety.

FIELD

Secure ligament graft constructs as well as systems and methods for preparing such ligament graft constructs are provided.

BACKGROUND

A ligament is a piece of fibrous tissue which connects one bone to another within the body. Ligaments are frequently damaged (e.g., detached, torn or ruptured) as the result of injury or accident. A damaged ligament can impede proper stability and motion of a joint and cause significant pain. A damaged ligament can be replaced or repaired using various procedures, a choice of which can depend on a particular ligament to be restored and on the extent of the damage. When ligaments are damaged, surgical reconstruction can be necessary, as the ligaments may not regenerate on their own.

An example of a ligament that is frequently damaged as a result of injury, overexertion, aging and/or accident is the anterior cruciate ligament (ACL) that extends between a top of the tibia and a bottom of the femur. Another ligament that is often damaged and may need to be replaced is a posterior cruciate ligament (PCL). A damaged ACL or PCL can cause instability of the knee joint, arthritis, and substantial pain.

ACL repair typically includes the use of a ligament graft replacement procedure which usually involves drilling a bone tunnel through the tibia and up into the femur. Then a ligament graft, which may be an artificial ligament or harvested graft, such as a tendon, is passed through a tibial portion of the tunnel (sometimes referred to as "the tibial tunnel") across the interior of the joint, and up into a femoral portion of a tunnel (sometimes referred to as "the femoral tunnel"). One end of the ligament graft can then be secured in the femoral tunnel and another end of the graft is secured in the tibial tunnel, at the sites where the natural ligament attaches.

A common ligament reconstruction procedure involves using an autograft, which is a portion of the patient's own tendon that would replace the damaged natural ligament. The autograft is often a hamstring tendon, though other tendons can be used (e.g., a patellar tendon). The ligament graft can also be obtained from a donor ("allograft").

Ligament augmentation and replacement procedures typically require preparation of a harvested ligament graft using various techniques to secure the graft for passing through the drilled tunnels and to strengthen the graft prior to fixation. The preparation may involve cleaning and measuring the graft, and then affixing sutures to free ends thereof. The thus prepared graft can be tensioned prior to being inserted into the femoral and tibial tunnels.

Various techniques for graft preparation exit, which have advantages and certain drawbacks. For example, sutures may be applied in such a manner that they cut through the tendon thus causing trauma to the graft. One cause of this phenomenon is that the tension may not be distributed uniformly along the length of the stitching. This, as well as other issues with graft preparation techniques, can cause the graft to deform and to be subjected to undesirable excessive elongation when a load is applied thereto. Furthermore, many of the conventional approaches are complicated and may therefore take up a significant portion of time of a surgery.

Accordingly, there is a need for improved graft constructs and techniques for preparing such graft constructs.

SUMMARY

A method of graft preparation is provided that in some embodiments can include (a) positioning a reinforcement ribbon over a first surface of a graft, the reinforcement ribbon being oriented to extend from a first end of the graft along a portion of a length of the graft toward an intermediate portion of the graft, the reinforcement ribbon having at least one suture tail extending therefrom; (b) passing a needle attached to the at least one suture tail through the reinforcement ribbon and through the first surface of the graft at a first entry point to a second, opposite surface of the graft; (c) passing the needle and the attached at least one suture tail around a side surface of the graft and passing the needle and the attached at least one suture tail through the reinforcement ribbon and the first surface of the graft at a second entry point, the second entry point being longitudinally spaced apart in a first direction from the first entry point; and (d) repeatedly passing the needle and the attached at least one suture tail around the side surface of the graft and through the reinforcement ribbon and the first surface of the graft at subsequent entry points longitudinally spaced apart in the first direction from the first and second entry points until a final entry point is in proximity to the first end of the graft.

The method of graft preparation can vary in any number of ways. For example, in one aspect, the first direction is in a direction from the intermediate portion of the graft to the first end of the graft. Further, in one aspect, steps (c) and (d) include passing the needle and the attached at least one suture tail around the same side surface of the graft. In another aspect, steps (c) and (d) include passing the needle and the attached at least one suture tail around opposed side surfaces in a sequential and alternating manner.

The suture tails can also vary in any number of ways. For example, in some embodiments, the at least one suture tail includes a first suture tail extending from a first end of the reinforcement ribbon and a second suture tail extending from a second, opposite end of the reinforcement ribbon.

In other embodiments, the at least one suture tail includes first and second suture tails extending from a same end of the reinforcement ribbon, the at least one suture tail having a needle attached thereto. In such embodiments, step (c) of passing the needle and the attached at least one suture tail around a side surface of the graft and passing the needle and the attached at least one suture tail through the reinforcement ribbon and the first surface of the graft at a second entry point includes passing the needle and the attached first and second suture tails around the first end of the graft so that the first end of the graft is passed through a loop formed by the first and second suture tails having the needle attached thereto. When the needle and the attached first and second suture tails are passed through the reinforcement ribbon and the first surface of the graft at the second entry point, the first and second suture tails form respective loops positioned on opposite side surfaces of the graft.

The reinforcement ribbon and the at least one suture tail can be integrally formed from a same suture.

In some embodiments, the method includes positioning a second reinforcement ribbon over the first surface of the graft, the second reinforcement ribbon being oriented to extend from a second, opposite end of the graft along a portion of a length of the graft toward the intermediate portion of the graft, the second reinforcement ribbon having at least one second suture tail extending therefrom. The method further includes passing a needle attached to the at least one second suture tail through the second reinforcement ribbon and through the first surface of the graft at a third entry point to the second surface of the graft, and performing steps (c)-(d) with the needle and the at least one second suture tail attached thereto.

In some embodiments, the method further includes using a guide in association with the reinforcement ribbon and the graft, the guide being movably positionable along the graft and the reinforcement ribbon so that an opening formed in the guide is disposed over a first portion of the reinforcement ribbon such that the needle and the attached at least one suture tail are passed through the opening.

The method of using the guide in association with the reinforcement ribbon and the graft can vary in a number of ways. For example, the method further includes positioning the guide so that at least a portion of the guide is disposed around the reinforcement ribbon and the opening is movably disposed approximately half-way between opposed side surfaces of the graft. For another example, the method further includes advancing the guide in the first direction along the reinforcement ribbon so as to change a position of the opening along a longitudinal axis of the reinforcement ribbon as the needle and the attached at least one suture tail are passed around the side surface of the graft and through the reinforcement ribbon and the first surface of the graft at entry points subsequent to at least one of the first and second entry points.

In some aspects, a tissue repair construct is provided that includes a graft material having first and second ends, a reinforcement material, and a suture secured to the reinforcement material and the graft material. The reinforcement material is positioned on a first surface of the graft material adjacent to the first end of the graft material, the reinforcement material having a first end adjacent to the first end of the graft material and a second end remote from the first end of the graft material. The suture is secured to the reinforcement material and the graft material, the suture forming multiple loops along a length of the reinforcement material and the graft material, each loop including a segment of the suture extending through the reinforcement material and through the first surface of the graft material at a first position to a second surface of the graft material, around a side portion of the graft material and through the reinforcement material and the first surface of the graft material at a position longitudinally spaced from the first position and exiting the second surface of the graft material. The tissue repair construct has at least one loose suture tail extending from the first end of the graft material.

The tissue repair construct can vary in a number of ways. For example, the reinforcement material can be formed integrally with the suture. For another example, the suture includes a first suture tail extending from the second end of the reinforcement material and a second suture tail extending from the first end of the reinforcement material. For another example, the suture includes first and second suture tails extending from a same end of the reinforcement material.

In some embodiments, a second reinforcement material is positioned on the first surface of the graft material adjacent to the second end of the graft material, the second reinforcement material having a first end adjacent to the second end of the graft material and a second end remote from the second end of the graft material. A second suture is secured to the second reinforcement material and the graft material, the second suture forming multiple loops along a length of the second reinforcement material and the graft material, each loop including a segment of the second suture extending through the second reinforcement ribbon and through the first surface of the graft material at a third position to the second surface of the graft material, around a side portion of the graft material and through the reinforcement material and the first surface of the graft material at a position longitudinally spaced from the third position and exiting the second surface of the graft material. The tissue repair construct has at least one loose second suture tail extending from the second end of the graft material.

In one aspect, a method of graft preparation that includes positioning a reinforcement ribbon over a first surface of a graft such that a first end of the reinforcement ribbon is adjacent a first end of the graft and the reinforcement ribbon extends along a portion of a length of the graft toward an intermediate portion of the graft, the reinforcement ribbon having at least one suture tail extending from a second, opposite end of the reinforcement ribbon. The method further includes positioning a guide member over the reinforcement ribbon and the graft such that an opening formed in the guide member is positioned over the reinforcement ribbon along a longitudinal axis of the reinforcement ribbon, and forming a plurality of loops along a length of the reinforcement ribbon and the graft. The plurality of loops are formed by forming each loop by passing the at least one suture tail through the opening so that the at least one suture is passed through the reinforcement ribbon and through the first surface of the graft at the first position to a second surface of the graft, around a side of the graft and through the reinforcement ribbon and the first surface of the graft at the second position longitudinally spaced from the first position in a first direction and exiting the second surface of the graft material, and, after the loop is formed, advancing the guide member in the first direction along the longitudinal axis of the reinforcement ribbon and the graft so that the at least one suture tail can be passed through the opening at a subsequent position spaced apart in the first direction from the first and second positions.

The method of graft preparation can vary in any number of ways. For example, the first direction can be in a direction from the intermediate portion of the graft to the first end of the graft. For another example, the method can include forming the loop by passing the at least one suture tail around opposed side surfaces in a sequential and alternating manner.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to systems and methods for preparing ligament grafts for ligament reconstruction or augmentation surgeries. A graft is prepared by reinforcing one or both end portions thereof to thus create a tissue repair construct. In some embodiments, a method is provided that includes preparing the tissue repair construct using a reinforcement material having one or more suture ends extending therefrom. The reinforcement material can be a ribbon or ribbon-like portion attached to or integrally formed with the one or more suture ends which can extend from one or both sides of the reinforcement material.

The reinforcement material is positioned on a first surface of a graft adjacent to a first end of the graft, and a needle having one or more suture ends coupled thereto is repeatedly passed through both the reinforcement material and the first and second surfaces of the graft and around a side surface of the graft so as to form multiple loops or stitches of the tissue repair construct. The thus formed loops serve to reinforce a portion of the graft extending from its first end. Another tissue repair construct can be formed on a second, opposite end of the graft.

The systems and methods described herein have a number of advantages over existing techniques for preparing ligament grafts. In particular, a graft is prepared using the described tissue repair construct in a simple and effective manner. For example, the suture loops passing through the reinforcement material and the graft can be made more quickly as compared to a locking whip-stitching. At the same time, the use of the reinforcement material allows the formation of a tissue repair construct of a strength and durability comparable to or exceeding that of a construct prepared with a locking whip-stitching. The reinforcement material protects the tissue of the graft and holds the multiple suture loops together so that, when a load is applied to the graft having the construct, excessive stretching of the graft and an impact of a cheese-wiring effect on the graft are prevented or decreased. As a result, a risk of damaging the graft can be reduced. Also, the amount of time required to prepare the graft can be reduced, which can facilitate the surgery and mitigate inconvenience to the patient. The described graft preparation procedure is simplified and is less labor-intensive. In addition, the described techniques can help to save operating room costs.

The described techniques can be used in conjunction with a variety of ligament grafts, including hamstring ligament grafts, in a variety of different surgical contexts regardless of the type of ligament graft being used in a particular surgical procedure. The systems and methods described herein can be utilized in connection with preparing grafts for repairing or replacing ligaments in a variety of joints. In some embodiments, the systems and methods described herein have particular utility in cruciate ligament reconstruction procedures. In some embodiments, the systems and methods described herein can be utilized for preparing ligament grafts for reconstruction procedures such as, for example, the cruciate ligaments of the knee.

Figure 1:
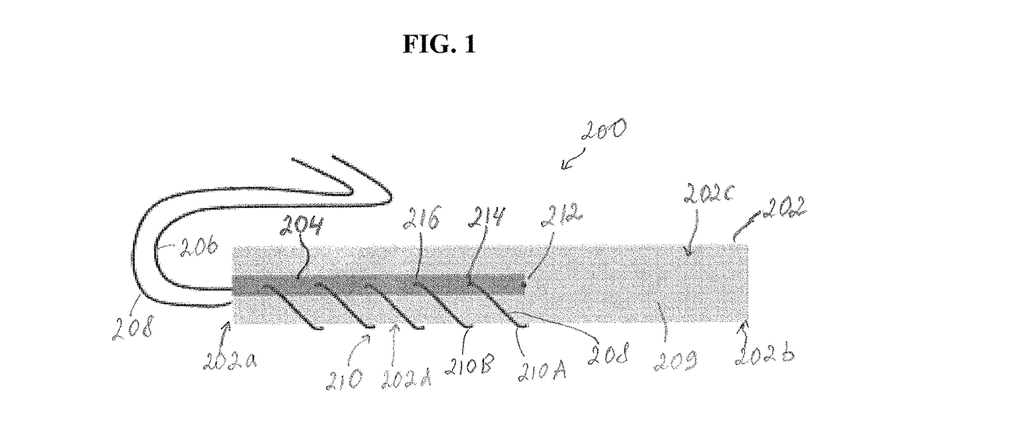
FIG. 1 is a schematic illustration of a tissue repair construct prepared in accordance with some embodiments.

FIG. 1 shows a tissue repair construct 200 in accordance with some embodiments. The tissue repair construct 200 includes a graft 202 having first and second ends 202a, 202b, and a reinforcement material 204 having first and second suture ends or tails 206, 208 attached thereto. A suture, for example, the second suture tail 208, is secured to the graft 202 and reinforcement material 204 and forms multiple loops 210, as discussed in more detail below.

The graft 202 can be a tendon or any other type of graft. The reinforcement material 204 and the second suture 208 affixed to both the reinforcement material 204 and the graft 202 provide structural support to the graft 202.

Figure 3:
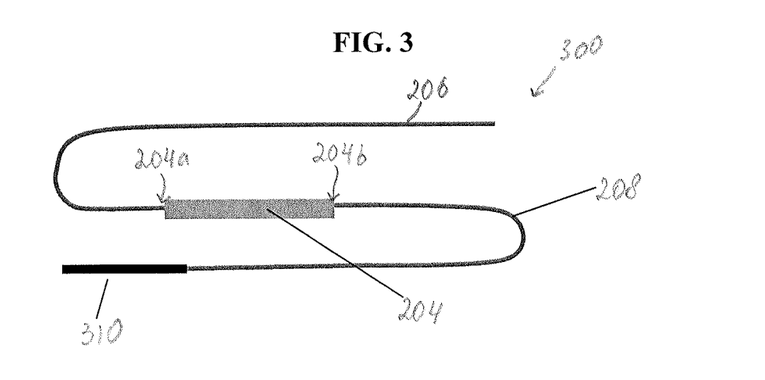
FIG. 3 is a schematic illustration of one embodiment of a reinforcement construct.

As also shown in FIG. 3, the first suture tail 206 extends from a first end 204a of the reinforcement material 204 and the second suture tail 208 extends from a second end 204b of the reinforcement material 204. In the illustrated embodiment, the reinforcement material 204 is positioned on a first surface 209 of the graft 202 so that the reinforcement material 204 is oriented to extend from the first end 202a of the graft 202 along a portion of a length of the graft 202 toward an intermediate portion 202c of the graft 202. A second surface of the graft 202 that is opposite to the first surface 209 thereof is not shown in FIG. 1. As shown in FIG. 1, the first end 204a of the reinforcement material 204 is adjacent the first end 202a of the graft 202 and the second end 204b of the reinforcement material 204 is remote from the first end 202a of the graft 202.

As shown in FIG. 1, in the illustrated embodiment, a suture including the second suture tail 208 is secured to the graft 202 and the reinforcement material 204 positioned on the graft 202 so as to form multiple loops 210 along a portion of the length of the reinforcement material 204 and the graft 202. In FIG. 1, two of the loops 210 are shown as loops 210A, 210B.

Each of the loops 210 includes a segment of the suture extending through the reinforcement material 204 and through the first surface 209 of the graft 202 at a first position to a second surface (not shown) of the graft 202, around a side portion of the graft 202 and then through the reinforcement material 204 and the first surface 209 of the graft 202 at a subsequent position longitudinally spaced apart from the first position and exiting the second surface of the graft 202. For example, the first loop 210A includes a segment of the suture extending through the reinforcement material 204 and through the first surface 209 of the graft 202 at a first position 212 to a second surface (not shown) of the graft 202, around a side portion 202d of the graft 202 and then through the reinforcement material 204 and the first surface 209 of the graft 202 at a next, second position 214 longitudinally spaced apart from the first position 212 and exiting the second surface of the graft 202.

In a similar manner, the second exemplary loop 210B is formed by a segment of the suture 208 extending through the reinforcement material 204 and through the first surface 209 of the graft 202 at the second position 214 to the second surface (not shown) of the graft 202, around the side portion 202d of the graft 202 and then through the reinforcement material 204 and the first surface 209 of the graft 202 at a next, third position 216 longitudinally spaced apart from the first and second positions 212, 214 and exiting the second surface of the graft 202. Other loops 210 form segments in the similar manner. As shown in FIG. 1, in the complete tissue repair construct 200, the loose first suture end 206, as well as the loose end of the second suture 208 used to form the loops 210, extend from the first end 202a of the graft 202.

One skilled in the art will appreciate that five loops 210 formed from the second suture tail 208 are shown by way of example only, as the tissue repair construct 200 can include any number of suture loops 210. Furthermore, one skilled in the art will also appreciate that, in some embodiments, the reinforcement material 204 can have a length such that it spans about half of the total length of the graft 202. In this case, the second end 204b of the reinforcement material 204 is positioned in proximity to the intermediate portion 202c of the graft 202. However, in other embodiments, the length of the reinforcement material 204 is less than half of the length of the graft 202 so that the second end 204b of the reinforcement material 204 extends toward but does not reach the intermediate portion 202c of the graft 202. One skilled in the art will appreciate that the reinforcement material 204 can have any suitable length and can extend from an end of the graft 202 along any portion of the length thereof, as the described embodiments are not limited in this respect.

Although not shown in FIG. 1, the second end 202b of the graft 202 that is opposite to the first end 202a of the graft 202 can have a tissue repair construct formed thereon. In this way, both ends 202a, 202b of the graft 202 can be reinforced using the described techniques.

Figure 2:
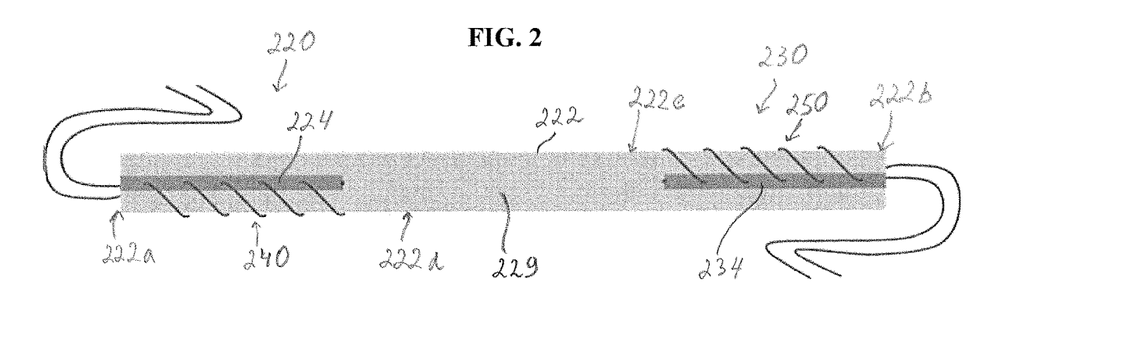
FIG. 2 is a schematic illustration of a graft having a tissue repair construct prepared on both ends thereof in accordance with some embodiments.

FIG. 2 illustrates one example of a graft 222 having tissue repair constructs 220, 230 formed on first and second ends 222a, 222b thereof. As shown, reinforcement constructs 224, 234 having respective suture tails extending therefrom are positioned over a surface 229 of the graft 222 to extend towards opposite ends 222a, 222b of the graft 202. Each of the reinforcement constructs 224, 234 can extend from any point (entry point for a suture) on the surface of the graft.

As shown in FIG. 2, multiple suture loops 240 are formed by passing a suture tail attached to the reinforcement construct 224 through the surface 229 of the graft 222 and the reinforcement construct 224 and, similarly, multiple suture loops 250 are formed by passing a suture tail attached to the reinforcement construct 234 through the surface 229 of the graft 222 and the reinforcement construct 234. The tissue reinforcement constructs 224, 234 can have any suitable lengths, including different lengths, and the suture loops 240, 250 can include any suitable number of loops. In the illustrated exemplary embodiment, the suture loops 240, 250 are formed by passing respective sutures around opposite side surfaces 222d, 222e of the graft 222. However, one skilled in the art will appreciate that the suture loops 240, 250 can be formed by passing the suture around the same side surface (e.g., the side surface 222d or the side surface 222e) of the graft 222.

Furthermore, although in the illustrated embodiment similar tissue repair constructs 220, 230, which can both be similar to tissue repair construct 200 in FIG. 1, are formed on the opposite end portions of the graft 222 terminating at the first and second ends 222a, 222b, these end portions can be reinforced using other types of tissue repair constructs. For example, tissue repair construct 600 (FIG. 6) or 700 (FIG. 7), or other constructs can be formed on both ends of a graft. End of a graft can be reinforced using the same type of tissue repair constructs or different tissue repair constructs.

FIG. 3 illustrates one embodiment of a reinforcement construct 300 prior to it being secured to a graft material to prepare the graft material for a surgical procedure. In the illustrated exemplary embodiment, the reinforcement construct 300 includes a reinforcement material, such as reinforcement material 204 of FIG. 1, having at least one suture tail extending therefrom. As shown, a first suture tail 206 extends from a first end 204a of the reinforcement material 204, and a second suture tail 208 extends from a second end 204b of the reinforcement material 204. One of the first and second suture tails 206, 208, e.g., in this example, the second suture tail 208, has a needle 310 coupled thereto. The second suture tail 208 can be passed through an eyelet (not shown) in the needle 310 or it can otherwise be coupled to the needle 310. The needle 310 having the second suture tail 208 attached thereto can be passed through both the reinforcement material and the graft, as discussed in more detail with regard to FIGS. 5A-5D.

The reinforcement construct 300 can have any suitable configuration. In the illustrated embodiment, the reinforcement construct 300 includes a flat or flattened portion forming the reinforcement material 204. The reinforcement material or portion 204 can be a ribbon or a ribbon-like feature and it can be formed integrally with the first and second suture tails 206, 208.

In some embodiments, the reinforcement material 204 and the first and second suture tails 206, 208 are formed from a single suture. For example, the reinforcement material 204 can be formed by braiding, crocheting, knitting, weaving, entangling, or otherwise forming the ribbon-like portion of the reinforcement material 204. In one embodiment, the reinforcement material can be formed by braiding along the length of the suture, for example, by alternating between a round, hollow portion and a flat, wider, ribbon-like section. Alternatively, the reinforcement material or portion can be created by physically flattening a portion of the suture, e.g., by a combination of compression and heat treatment. Any other suitable technique can be used to flatten a portion of the suture to form the reinforcement portion.

In some embodiments, the reinforcement portion is created by crocheting a chain at a midsection of a single strand of suture. As another example, the reinforcement portion can be an integral part of the suture such that the reinforcement portion is identified in a suitable manner (e.g., marked) along a length of the suture. This can be performed using a guide that helps to pass the needle through the reinforcement portion, as discussed below.

In some embodiments, one or more additional sutures or other material(s) can be used to form the reinforcement material 204. For example, suture(s) or individual filaments of a suture can be axially incorporated into the suture forming reinforcement material 204 to control the strength thereof.

In other embodiments, the reinforcement material 204 and one or both of the first and second suture tails 206, 208 are formed from separate elements or pieces. For example, the reinforcement material portion 204 can be formed from one material, whereas one or both of the first and second suture tails portions 206, 208 can be formed from a different material and/or different elements. In such embodiments, one or both of the first and second suture tails 206, 208 can be securely attached to the reinforcement material 204, e.g., stitched, stapled, glued, or otherwise attached in a suitable manner.

The reinforcement construct 300 and its components can have any suitable dimensions. As discussed above, the reinforcement material 204 has a length so that the reinforcement material 204 is configured to be positioned to extend from an end of a graft toward an intermediate portion of the graft. The length of the reinforcement material 204 can vary depending on various factors, such as patient's characteristics, properties of the graft, the type of the injury, and/or any other factors. In one embodiment, the reinforcement material 204 extends along a portion of a length of the graft that does not exceed a half-length of the graft.

The length of the reinforcement material 204 can range from about 10 millimeters (mm) to about 60 mm, and the length of each of the first and second suture tails 206, 208 can range from about 5 inches to about 25 inches. In embodiments in which one of the suture tails is secured to the graft and the reinforcement material, a length of that suture tail can be selected so that initially the tail is longer than another tail and, after the suture is attached to the graft and the reinforcement material, loose suture ends extending from an end of the reinforcement material have the same or approximately the same length.

The reinforcement material 204 can have any suitable width. In one embodiment, the width of the reinforcement material 204 is such that the reinforcement material 204 is configured to be positioned on a surface of the graft without reaching the opposite sides of the graft. Thus, the width of the reinforcement material 204 is narrower than the width of the graft. For example, the width of the reinforcement material 204 can range from about 0.5 mm to about 5 mm. In one exemplary embodiment, the width of the reinforcement material 204 ranges from about 2 mm to about 3 mm.

The reinforcement construct 300 can be formed from any suitable material or a combination of materials. In one embodiment, the reinforcement construct 300 is formed from Ethibond™ No. 2 suture. The reinforcement material 204 can be formed from the same or different material that is used to form the suture tails. For example, in some embodiments, the reinforcement material 204 is formed from Ethibond™ No. 5 suture while the suture tails are formed from Ethibond™ No. 1 suture or Ethibond™ No. 2 suture. One skilled in the art will appreciate that the reinforcement construct 300 can additionally or alternatively be formed from any other type of suture.

Sutures comprising any suitable materials can be used for the described graft preparation techniques. In some embodiments, one or more components of the tissue reinforcement construct can include various surgical sutures, typically size 0 to size 5, such as Orthocord™ suture commercially available from DePuy Mitek, and Ethibond™ suture available from Ethicon, Inc. Orthocord™ suture is approximately fifty-five to sixty-five percent PDS™ polydioxanone, which is bioabsorbable, and the remaining percent ultra high molecular weight polyethylene, while Ethibond™ suture is primarily high strength polyester. In some embodiments, the reinforcement construct can be formed from ultra-high-molecular-weight polyethylene (UHMWPE). In some embodiments, the construct can include High-Molecular Weight-polyethylene (HMWPE) sutures or HMWPE sutures with a co-braid (e.g., monofilament polypropylene, nylon or other co-braid). In some embodiments, monofilament sutures such as, for example, Monocryl® available from Ethicon, Inc., may be utilized. As another example, an absorbable suture such as Vycryl® (a copolymer made from 90% glycolide and 10% L-lactide) also available from Ethicon, Inc. may be used. The sutures used herein can have any suitable amount and type of bioabsorbable material, which can depend on a particular surgical procedure and/or surgeon preferences.

Figure 4:
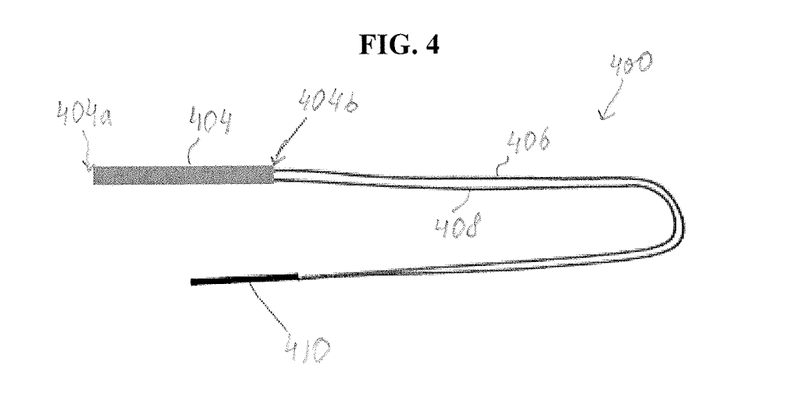
FIG. 4 is a schematic illustration of another embodiment of a reinforcement construct.

It should be appreciated that at least one suture tail can extend from one or both ends of the reinforcement material. Thus, FIG. 4 illustrates one embodiment of a reinforcement construct 400 including a reinforcement material 404, which has first and second ends 404a, 404b, having first and second suture tails 406, 408 extending from the second end 404b thereof. As shown in FIG. 4, in the reinforcement construct 400, the first and second suture tails 406, 408 are attached to a needle 410. The first and second suture tails 406, 408 can be passed through an eyelet in the needle 410, crimped into the needle 410, or otherwise attached to the needle.

The first and second suture tails 406, 408 can be formed in any suitable manner. In one embodiment, the first and second suture tails 406, 408 can be formed from the same suture that is used to form the reinforcement material 404. For example, the first and second suture tails 406, 408 can be formed from a single suture so that they extend from the same bifurcation point at the second end 404b of the reinforcement material 404, whereas the reinforcement material 404 can be formed by braiding, weaving, knitting, crocheting, flattening, or otherwise manipulating that suture. In other embodiments, the reinforcement material 404 and at least one of the first and second suture tails 406, 408 are formed from separate elements attached to each other in a suitable manner. The reinforcement material 404 can be formed from various materials and can be sized in various ways, as discussed above with regard to the reinforcement material 204 in FIGS. 1 and 3.

FIGS. 5A-5D illustrate schematically a method of preparation of a graft 502 using a reinforcement construct 500 similar to reinforcement construct 300 of FIG. 3, to create a tissue repair construct in accordance with some embodiments. The graft 502 can be obtained either from the patient with the diseased or damaged ligament ("autograft") or from a donor ("allograft"). The graft 502 can include one or more tendon strands or it can be any other type of graft. The graft 502 can be cleaned, sized, and processed in a suitable way prior to affixing sutures thereto in accordance with the described techniques.

Figure 5A:
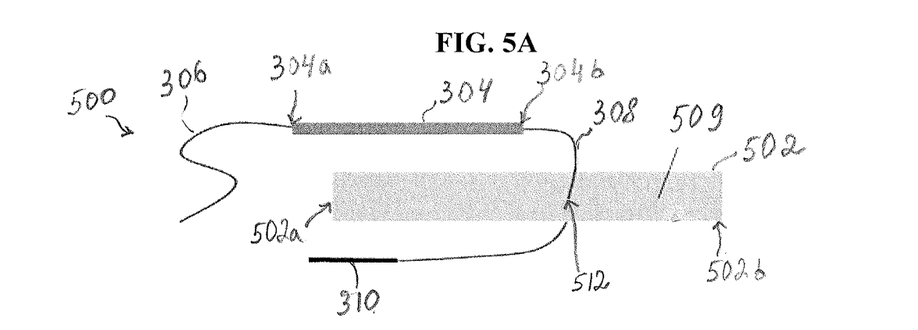
FIGS. 5A-5D are schematic illustrations of one embodiment of a method of preparing a tissue repair construct.

As shown in FIG. 5A, the graft 502 has first and second ends 502a, 502b. In the illustrated embodiment, the first end 502a is a proximal end and the second end 502b is a distal end. As used herein, the "proximal" end is defined as an end of the graft 502 that is nearest surgeon's hands preparing the graft 502. The "distal" end is defined as an opposite end of the graft 502 which can be fixed using, for example, suitable graft preparation equipment (not shown). Alternatively, in some cases, the distal end 502b of the graft 502 can remain attached to the donor site of obtaining the graft 502 so that the graft 502 is prepared for the reconstruction surgery without being separated from that site.

Furthermore, one skilled in the art will understand that the first and second ends 502a, 502b are referred to as "proximal" and "distal," respectively, only to indicate that the first end 502a of the graft 502 is an end to which the reinforcement construct 300 extending therefrom is being secured. Because both ends of the graft 502 can be reinforced with a reinforcement construct, such as the reinforcement construct 300, when the reinforcement construct 300 is secured to the second end 502b of the graft 502, the second end 502b will be referred to as the proximal end and the first end 502a will be referred to as the distal end. It should be appreciated that one or both ends of the graft 502 can be attached to suitable graft preparation equipment.

Referring back to FIG. 5A, in the illustrated embodiment, the reinforcement construct 500 includes a reinforcement material or reinforcement ribbon 304, which can be similar to reinforcement material 204 in FIGS. 1 and 3, having first and second suture tails 306, 308 extending from first and second ends 304a, 304b thereof, respectively. As shown, a needle 310 is attached to the second suture tail 308 in a suitable manner.

Figure 5B:
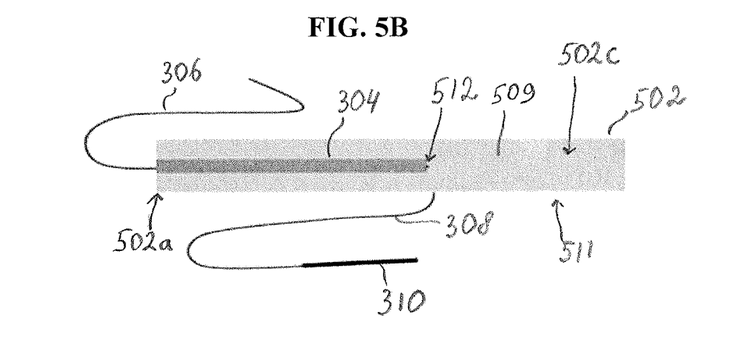

The reinforcement ribbon 304 is positioned over a first surface 509 of the graft 502. As shown in FIG. 5B, the reinforcement ribbon 304 is oriented to extend from the first end 502a of the graft 502 along a portion of a length of the graft 502 toward an intermediate portion 502c of the graft 502. The intermediate portion 502c may be located approximately mid-way between the first and second ends 502a, 502b of the graft 502. As also shown in FIG. 5B, the reinforcement ribbon 304 is positioned over the first surface 509 of the graft 502 so that the first end 304a of the reinforcement ribbon 304 is adjacent to or is aligned with the first end 502a of the graft 502 and the second end 304b of the reinforcement ribbon 304 is remote from the first end 502a of the graft 502. It should be appreciated that not the entire graft 502 is shown in FIGS. 5A-5D, so that the intermediate portion 502c of the graft 502 can be located further away from the first end 502a of the graft 502 than shown in FIGS. 5A-5D and approximately mid-way between the first and second ends 502a, 502b. In addition, as mentioned above, the reinforcement ribbon 304 can extend along a portion of the graft 502 that has a shorter length than the half-length of the graft 502.

Prior to or after positioning the reinforcement ribbon 304 along the graft 502 as shown in FIG. 5B, the needle 310 having the second suture tail 308 attached thereto is passed through the first surface 509 of the graft 502 at a first entry point 512 to a second, opposite surface 511 of the graft 502. As shown in FIGS. 5A and 5B, the needle 310 and the attached second suture tail 308 are passed through the reinforcement ribbon 304 and the first surface 509 of the graft 502 at the first entry point 512 so that substantially the entirety of the second suture tail 308 is passed to the second surface 511 of the graft 502 and extends therefrom. As used herein, "substantially" indicates that only a small portion or no portion of the second suture tail 308 remains on the first surface 509 of the graft 502. The reinforcement ribbon 304 remains positioned on the first surface 509 of the graft 502.

Figure 5C:
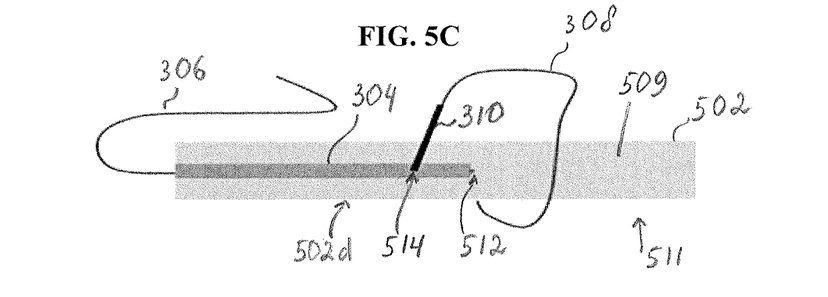

As shown in FIG. 5C, next, the needle 310 with the attached second suture tail 308 is passed around a side surface 502d of the graft 502. The needle 310 with the attached second suture tail 308 is then passed through the reinforcement ribbon 304 and the first surface 509 of the graft 502 at a second, subsequent entry point 514 to the second surface 511 of the graft 502. In this way, a first loop of the loops 510 is formed as shown in FIG. 5D.

Figure 5D:
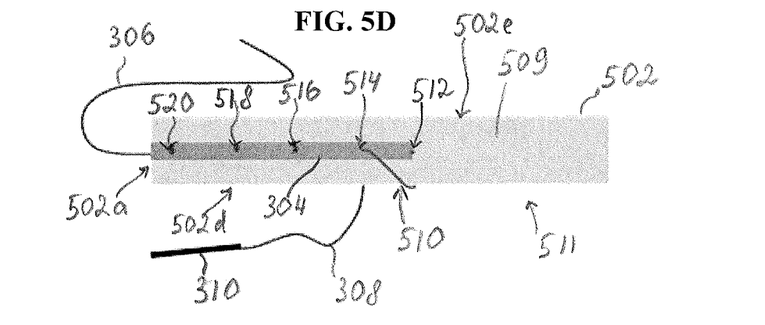

As shown in FIGS. 5C and 5D, the second entry point 514 is longitudinally spaced apart in a first direction from the first entry point 512. In the illustrated embodiment, the first direction is a direction from the intermediate portion 502c of the graft toward the first end 502a of the graft 502. The process can continue in a similar manner, so that the needle 310 with the attached second suture tail 308 is repeatedly passed around the side surface 502d of the graft 502 and through the reinforcement ribbon 304 and the first surface 509 of the graft 502 at subsequent entry points 516, 518, 520, longitudinally spaced apart in the first direction from the first and second entry points 512, 514 until a final entry point 520 is in proximity to the first end 502a of the graft 502. In this way, multiple loops similar to the loop 510 in FIG. 5D are created so that, in some embodiments, the resulting tissue repair construct similar to tissue repair construct 200 shown in FIG. 1 is formed.

It should be appreciated that the entry points 512-520 are shown by way of example only, to illustrate that each entry point after the first entry point 512 is spaced apart from a previous entry point at approximately the same distance. In one embodiment, the reinforcement ribbon 304 can have one or more markings indicated one or more of the entry points 514-520. However, in other embodiments, the markings need not be used. The distance between the entry points depends, for example, from a desirable number of loops to be formed on the graft 502 and the reinforcement ribbon 304. The larger the number of loops formed, the more securely the suture is attached to the reinforcement ribbon 304 and the graft 502. However, as the number of loops increase, so does the potential to damage the graft 502. Thus, the number of loops can be selected to ensure that the suture is attached sufficiently strongly to the reinforcement ribbon 304 and the graft 502 while not causing excessive damage to the tissue of the graft 502. The number of loops ranges from 2 to 10 loops, or, in some embodiments, from 3 to 5 loops. However, any suitable number of loops can be formed.

In some embodiments, the method of preparing a tissue repair construct involves passing the needle and the attached at least one suture tail around the same side surface of the graft. For example, as shown in FIGS. 5C and 5D, the needle 310 and the attached second suture tail 308 are passed around the side surface 502d of the graft 502. As a result, in the thus formed tissue repair construct (e.g., similar to tissue repair construct 200 in FIG. 1), all loops 510 will pass through the graft 502 and the reinforcement ribbon 304 and through the same side surface 502d of the graft 502. One skilled in the art will appreciate that the loops 510 can also be formed by passing the needle 310 and the attached second suture tail 308 around an opposite side surface 502e of the graft 502.

Figure 6:
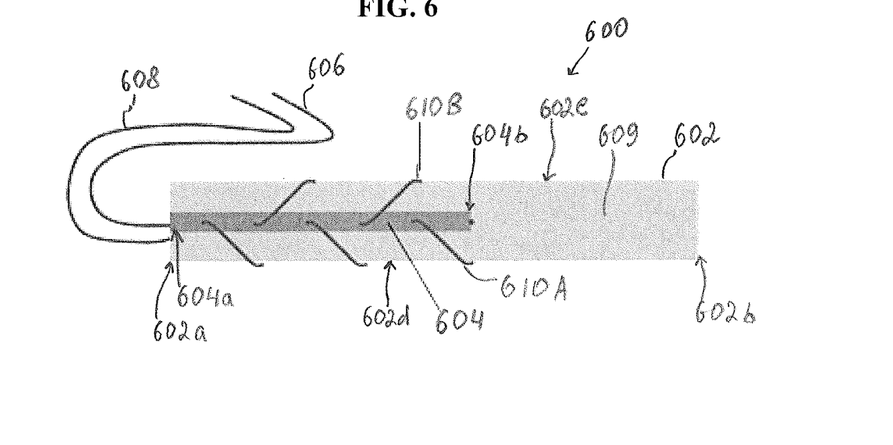
FIG. 6 is a schematic illustration of one embodiment of a tissue repair construct.

Furthermore, in some embodiments, a graft is reinforced using the described tissue reinforcement construct by passing a needle and an attached at least one suture tail around opposed side surfaces of the graft in a sequential and alternating manner. FIG. 6 illustrates one embodiment of a tissue repair construct 600 where suture loops are formed around alternating side surfaces of a graft 602.

As shown in FIG. 6, a graft 602 has a reinforcement material 604 positioned on a first surface 609 thereof, along a portion of a length of the graft 602 so that a first end 604a of the reinforcement material 604 is adjacent to or is aligned with a first end 602a of the graft 602. A second end 604b of the reinforcement material 604, remote from the first end 604a, is positioned nearer to an intermediate portion of the graft 602. Similar to first and second suture tails 306, 308 of reinforcement material 304 in FIGS. 5A-5D, first and second suture tails 606, 608 are attached to the first and second ends 604a, 604b of the reinforcement material 604, respectively.

Suture loops 610 can be formed in the same manner as shown in connection with FIGS. 5A-5D. For example, as shown in FIG. 6, after a suture attached to the reinforcement material 604 is passed through the graft at a first entry point, a first loop 610A is formed by passing a needle (not shown in FIG. 6) and the attached at least one suture tail (e.g., a second suture tail 608 in FIG. 6) around a side surface 602d of the graft 602 and then by passing the needle with the second suture tail 608 through the graft 602 and the reinforcement material 604 at a second entry point. However, after the first loop 610A is formed in this manner and when the second suture tail 608 extends from a second surface of the graft 602 opposite to the first surface 609 thereof, the second suture tail 608 is passed around a side surface 602e of the graft 602, which is opposite to the side surface 602d thereof, and then through the graft 602 and the reinforcement material 604 at a third entry point. In this way, the second loop 610B is formed as shown in FIG. 6.

The remaining loops can be formed by repeatedly passing the needle and the attached at least one suture tail around alternating side surfaces 602d, 602e of the graft 602 so as to form the tissue repair construct 600 as shown in FIG. 6. As discussed above, a distance between subsequent entry points can be the same or it can vary.

Figure 7:
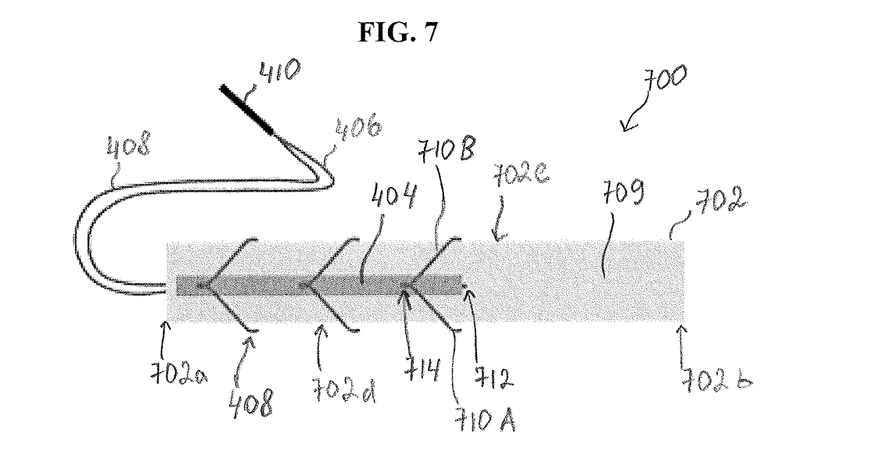
FIG. 7 is a schematic illustration of one embodiment of a tissue repair construct prepared using the reinforcement construct of FIG. 4.

FIG. 7 illustrates another embodiment of a tissue repair construct 700 prepared using the described techniques. In this illustrative embodiment, a tissue reinforcement construct, such as reinforcement construct 400 shown in FIG. 4, is used. As discussed above, the reinforcement construct 400 includes reinforcement material 404 having both first and second suture tails 406, 408 extending from the same end (e.g., second end 404b) thereof. The ends of the first and second suture tails opposite to their ends coupled to (or formed integrally with) the reinforcement material 404 are attached to a needle 410 in a suitable manner, as shown in FIG. 4.

In one embodiment, the tissue reinforcement construct 400 is used to create the tissue repair construct 700 shown in FIG. 7. As shown in FIG. 7, the reinforcement material 404 can be positioned on a first surface 709 of the graft 702 so as to extend from a first end 702a thereof, along a portion of a length of the graft 702, similarly to the way in which reinforcement material 204 (FIG. 1), reinforcement material 304 (FIGS. 5B-5D), or reinforcement material 604 (FIG. 6) are positioned over a graft. Further, after the needle 410 with the attached suture tails 406, 408 is passed through the first surface 709 of the graft 702 to a second, opposite surface of the graft 702 at a first entry point 712, the needle 410 with the attached first and second suture tails 406, 408 is passed around a second end 702b of the graft 702 and then through the reinforcement material 404 and through the first surface 709 of the graft 702 at a second entry point 714. In this way, a loop (not shown) is formed by the suture tails 406, 408 attached to the needle, and the second end 702b of the graft 702 is passed through that loop. At the same time, the first and second suture tails 406, 408 are passed around respective opposite sides 702d, 702e of the graft 702.

Thus, piercing the reinforcement material 404 and the first surface 709 of the graft 702 with the needle having the first and second suture tails 406, 408 attached thereto at the second entry point 714 simultaneously forms loops 710A, 710B on respective opposite sides 702d, 702e of the graft 702, as shown in FIG. 7. The process can continue in the same manner by passing the needle with the first and second suture tails 406, 408 attached thereto around the second end 702b of the graft 702 and then through the reinforcement material 404 and the first surface 709 of the graft 702 at subsequent entry points. As a result, a tissue repair construct such as the tissue repair construct 700 shown in FIG. 7 can be formed.

After the preparation of the tissue repair construct 700 is complete, the first and second suture tails 406, 408 are cut to separate them from the needle 410 or the needle 410 is otherwise removed from the first and second suture tails 406, 408. As described with regard to other embodiments, after the tissue repair construct 700 is formed on one end of the graft 702 (the first end 702a, in this example), the same or similar tissue repair construct can be formed on an opposite end of the graft 702. Thus, although not shown, reinforcement material, such as, for example, reinforcement material 404, can be positioned to extend from the second end 702b of the graft 702 toward the intermediate portion of the graft 702, and a second tissue repair construct can be formed on the graft 702 to reinforce its second end.

It should be appreciated that, in some embodiments, different types of tissue repair constructs can be formed on opposite ends of a graft. For example, in one embodiment, one end of the graft can be prepared as a tissue repair construct such as tissue repair construct 200 (FIG. 1), whereas another end of the graft can be prepared as a different tissue repair construct, such as, e.g., tissue repair construct 600 (FIG. 6) or tissue repair construct 700 (FIG. 7). Other combinations of different types of constructs used to prepare a graft can be used as well.

Regardless of the type of a tissue repair construct utilized, the described techniques using a reinforcement material that has a suture passed therethrough allow the creation of a tissue repair construct that is at least as simple as the conventional whip-stitching and, at the same time, provides a strength and security of a locking stitch. The reinforcement material serves as a backbone for loops formed around one or both sides of the graft and links the loops together. When a load is applied to the graft, the load is distributed more evenly around the surface of the graft and overstretching of the loop closest to the load ("final loop") can be decreased. Furthermore, excessive stretching of the graft and an impact of a cheese-wiring effect on the graft can be prevented or decreased.

In some embodiments, a guide or a guide member is used to help to guide a needle to pierce through a reinforcement material positioned over a graft and through the graft. The guide member is a device associated with the reinforcement material or both the reinforcement material and the graft and allows directing the needle into a proper location on the surface of the reinforcement material. The guide member can be used during preparation of any type of a graft.

Furthermore, a graft can be narrow and the guide member directs a surgeon or other person holding a needle with the attached suture to insert the needle into appropriate locations along the surface of the reinforcement material extending over a surface of the graft.

Figure 8:
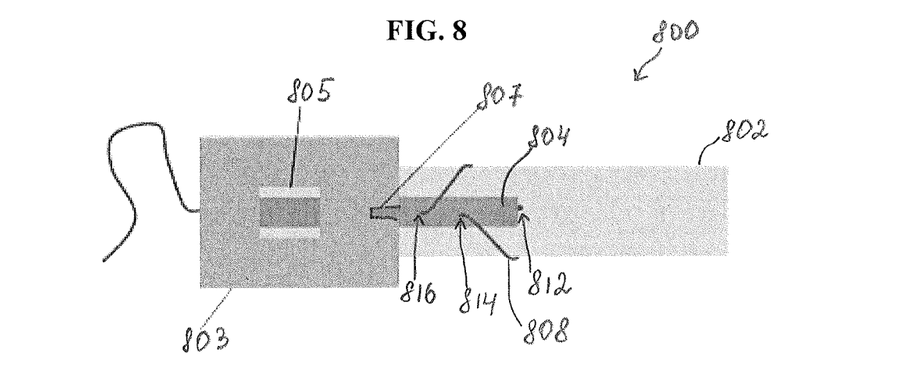
FIG. 8 is a schematic illustration of one embodiment of a guide used to prepare a tissue repair construct.

FIG. 8 illustrates one embodiment of a guide member used in association with a reinforcement construct used to create a tissue repair construct 800. As shown schematically in FIG. 8, a guide member 803 is associated with a reinforcement material 804 positioned over a graft 802. The reinforcement material 804 having first and second suture tails attached thereto can be similar to any of the reinforcement materials described herein, such as reinforcement materials 204, 304, 404, or 604. In the illustrated embodiment, the first and second suture tails extend from opposite ends of the reinforcement material 804, and the second suture tail 808 is used to form suture loops.

The guide member 803 can be associated with the reinforcement material 804 in any suitable manner. For example, the guide member 803 can be movably coupled to the reinforcement material 804 so that the guide member 803 can slide along the reinforcement material 804. In some embodiments, the guide member can be movably coupled to both the reinforcement material 804 and the graft 802. The guide member 803 can be associated with one or both of the reinforcement material 804 and the graft 802 so that one or more portions of the guide member 803 sit around one or both of the reinforcement material 804 and the graft 802.

The guide member 803 can have a variety of configurations. In the illustrated embodiment, as shown in FIG. 8, the guide 803 includes a feature, such as a first opening, 805 that allows controlling the position of the reinforcement material 804, and a second opening 807 that serves as a needle guide. In the illustrated embodiment, the first opening 805 can be used to control the position of the reinforcement material 804 relative to the needle guide 807.

The reinforcement material 804 can be positioned along a portion of a length of the graft so that a longitudinal axis of the reinforcement material 804 coincides with a longitudinal axis of the graft 802. The feature 805 may be configured so as to hold the reinforcement material 804 at a certain position along a surface of the graft 802 that has the reinforcement material 804 disposed thereon. That position is maintained as the surgeon slides the guide member 803 along the reinforcement material 804 during preparation of a tissue reinforcement construct, as subsequent suture loops are formed on the reinforcement material 804 and the graft 802. Although not shown in FIG. 8, the first opening 805 can include or can be associated with additional features that help to maintain a position of the reinforcement material 804 with respect to the graft 802. In embodiments in which the suture is passed through the graft in an approximately zigzag manner (e.g., as shown in FIG. 6), the guide member 803 allows the surgeon (or other medical professional) to move the graft in a transverse direction relative to the guide between forming consecutive suture loops.

It should be appreciated that the feature 805 is shown in the form of a rectangular opening by way of example only, as the feature 805 can be in the form of one or more openings having any suitable shape and size. The first opening 805 allows a surgeon or other medical professional to view a portion of the reinforcement material 804 through the opening 805 and to confirm that the reinforcement material 804 is properly aligned with the needle guide 807. However, it should be appreciated that the feature 805 is shown as having an opening by way of example only, as the feature 805 can have any other configuration, including a configuration without an opening.

As shown in FIG. 8, the guide member 803 also includes an opening or a needle guide 807. The opening 807 directs a surgeon holding a needle having the suture 808 attached thereto to an appropriate position along the reinforcement material 804. The guide member 803 can be positioned over the reinforcement material 804 before a first loop is formed. In one embodiment, the guide member 803 can be attached to the reinforcement material 804 before the reinforcement material 804 is positioned along the surface of the graft 802. The opening 807 is thus positioned so as to guide the surgeon to pierce the needle with the suture 808 through the opening 807 so that the needle with the suture 808 is passed through the graft 802 at a first entry point 812. In another embodiment, the guide member 803 is positioned so that the needle with the suture 808 is passed through the graft 802 at the first entry point 812 without the aid of the guide member 803, and the guide member 803 is used when the first and subsequent loops are created.

Regardless of whether the guide member 803 is used to guide the surgeon to pierce the graft 802 at the first entry point 812, after the needle with the suture 808 attached thereto is passed through the graft 802 at an initial entry point (e.g., point 812), the guide member 803 can be used to assist the surgeon in aiming a guiding end of the needle at any of the subsequent points along the reinforcement material 804. Once the needle with the suture 808 is passed around a side surface of the graft and through an entry point to thereby form a loop, the guide member 803 is moved so as to aim the needle with the suture, after it has been passed around a side surface of the graft, at a next entry point.

In some embodiments, the guide member 803 is used to control a distance between entry points at which the needle and the attached suture pass through the reinforcement material 804 and the graft 802. In such embodiments, the guide member 803 can be configured to move stepwise, so that it moves a certain distance from one point to another along the graft 802 and, once the guide member 803 is moved that distance, its position is locked or otherwise restrained to temporary prevent its further movement. The distance by which the guide member 803 moves at each step can be configurable. In this way, subsequent entry points can be disposed at desired (e.g., approximately equal) distances apart from each other. In one embodiment, a configuration of the guide member 803 allows the entry points to be spaced apart at approximately equal distances from each other.

Figure 9A:
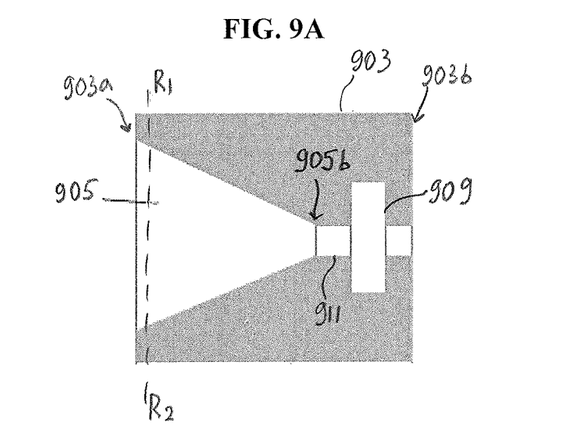
FIG. 9A is a perspective side view of another embodiment of a guide used to prepare a tissue repair construct.
Figure 9B:
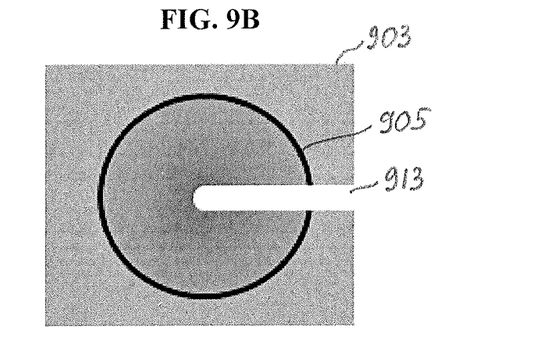
FIG. 9B is a perspective front view of the guide of FIG. 9A.
Figure 9C:
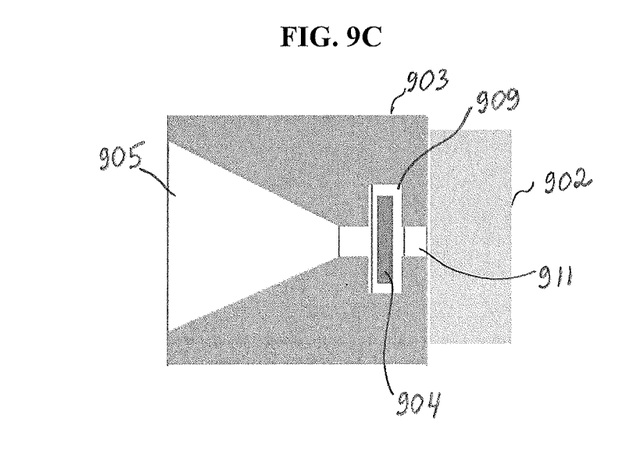
FIG. 9C is a perspective side view of the guide of FIG. 9A in association with a reinforcement material disposed over a surface of a graft.
Figure 9D:
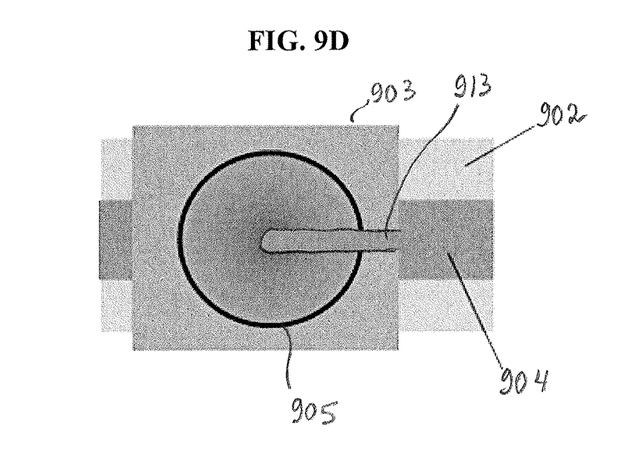
FIG. 9D is a perspective front view of the guide of FIG. 9B in association with a reinforcement material disposed over a surface of a graft.

FIGS. 9A-9D illustrate another embodiment of a guide member used during preparation of a tissue repair construct. The guide member can have a variety of configurations. As shown in FIG. 9A, illustrating a perspective side view of a guide member 903, the guide member 903 has a substantially rectangular body and a funnel-shaped opening 905 formed in the top surface 903a of the body so that the diameter of the opening 905 gradually decreases toward the bottom surface 903b of the guide member 903 that is positioned closer to the graft 902. The opening 905 is also shown in FIGS. 9B and 9D illustrating front views of the guide member 903 at a cross-section R1-R2 shown in FIG. 9A. One skilled in the art will appreciate that the guide member can have any other configuration, size, and shape. For example, in some embodiments, the guide member can be generally shaped as a funnel so that the walls of the funnel-shaped opening 905 form the body of the guide member 903.

In use, the surgeon passes a needle with at least one suture tail attached thereto through the top surface 903a of the funnel opening 905, as discussed in more detail below. The bottom portion of the funnel opening 905 is configured to be disposed around a portion of a reinforcement material or around both the reinforcement material and the graft. In the illustrated embodiment, as shown in FIG. 9A, the funnel opening 905 communicates at a bottom portion 905b thereof, via a connection portion 911, with a receiving portion or opening 909 that is configured to receive a reinforcement material 904 therein, as shown in FIG. 9C. The receiving portion 909 can have any configuration so that it receives at least a portion of the reinforcement material 904. In this way, the guide member 903 can be slidably positioned over the graft 902 so that at least a portion of the reinforcement material 904 is received by the receiving portion 909 to allow moving the guide member 903 along the graft 902 and the reinforcement material 904.

In the illustrated exemplary embodiment, as shown in FIG. 9C, the guide member 903 slidably sits around the reinforcement material 904 that is positioned over the graft 902. However, as mentioned above, in some embodiments, the guide member 903 is movably positioned around the graft 902 as well.

As shown in FIGS. 9B and 9D, the funnel opening 905 has a guide cutout 913, similar to opening 807 in FIG. 8, which allows the guide member 903 to move along the reinforcement material 904 after a loop is formed. As shown in FIG. 9D, the guide member 903 is positioned around the reinforcement material 904 disposed over the graft 902 so that the guide cutout 913 extends from the center of the opening 905 towards the edge of the guide member 903 in a direction towards an intermediate portion (not shown) of the graft 902. In other words, the guide cutout 913 leaves open a portion of a surface of the reinforcement material 904 which bears entry points at which the reinforcement material 904 and the graft 902 are pierced by a needle with a suture.

One skilled in the art will appreciate that the opening 905 is shown as having a funnel-like shape by way of example only. While such a shape facilitates aiming a needle into a desired location on the surface of the reinforcement material, openings having other shapes can be used additionally or alternatively. Furthermore, in some embodiments, the opening 905 can include additional surface features (e.g., on an inner wall thereof), such as, for example, prongs, fingers, or other protrusions that help to guide the needle toward an entry point on the reinforcement material.

The guide member can be formed from a plastic or other suitable material that is lightweight and therefore suitable for being placed over the reinforcement material during the graft preparation procedure as described herein. The material forming the guide member is also sufficiently rigid so that the guide member maintains its shape and is not unnecessary deformed during its use (e.g., when a needle is passed through its opening and/or as it is advanced along the graft). The guide member can be formed from any biocompatible metal (e.g., stainless steel) or plastic, such as polyetheretherketone (PEEK), acrylonitrile butadiene styrene (ABS), polycarbonate, or other material, or any combination of the above or other material(s).

The guide member described herein, such as guide member 803 or guide member 903, can be positioned over a reinforcement material during the preparation of the graft. Alternatively, the reinforcement material can be associated with the guide member as part of a preassembly of the reinforcement material.

FIGS. 10A-10E illustrate one embodiment of a method of preparing a tissue repair construct using a guide member, such as guide member 903. The tissue repair construct includes the reinforcement material 904 and the graft 902 shown in FIGS. 9C and 9D. However, one skilled in the art will appreciate that any reinforcement material in accordance with the described techniques can be used to reinforce any type of graft using the guide member 903 as a guiding aid.

Figure 10A:
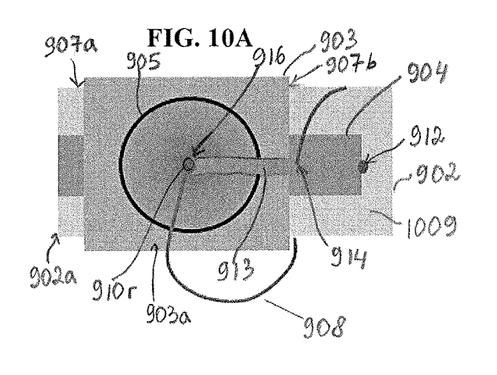
FIGS. 10A-10E are schematic illustrations of one embodiment of a method of using a guide to prepare a tissue repair construct.

In the illustrated example, the reinforcement material 904 has at least one suture tail extending therefrom, with only one suture tail 908 being shown in FIGS. 10A-10E. As shown in FIG. 10A, a needle 910 (shown in FIG. 10B) having the suture tail 908 attached thereto (which, in turn, is attached to the reinforcement material 904) is first passed through a first surface 1009 of the graft 902 at a first entry point 912 that defines a position of the reinforcement material 904 with respect to a first end 902a of the graft 902. The needle 910 then exits the graft 902 at a second, opposite surface 1011 of the graft 902. It should be appreciated that the needle 910 is shown schematically and that its forward end configured to pierce the reinforcement material and the graft is sharp.

As shown in FIG. 10A, after passing the graft 902 at the first entry point 912, the needle 910 with the suture tail 908 attached thereto passes the reinforcement material 904 at second and third entry points 914, 916. The guide member 903 is used to aim the needle 910 at entry points on a surface of the reinforcement material 904. Although FIG. 10A illustrates the guide member 903 positioned so that the guide cutout 913 exposes a location of the reinforcement material 904 where the third entry point 916 is formed, the guide member 903 can also be used to guide the needle 910 with the attached suture tail 908 to pierce through the first and second entry points 912, 914.

FIG. 10A illustrates that the guide member 903 is positioned over the reinforcement material 904 so that the center of the opening 905 is disposed over the location of the third entry point 916. The guide cutout 913 extends from the center of the opening 905 toward the intermediate portion of the graft 902, in a direction away from the first end 902a of the graft 902. The opening 905 is formed so that it is positioned along a longitudinal axis of the guide member 903 extending between first and second ends 907a, 907b of the guide member 903. The center of the opening 905 can be positioned approximately mid-way between the first and second ends 907a, 907b or it can be offset from a mid-point between the first and second ends 907a, 907b. As discussed above, the opening 905 is formed so that its diameter is gradually (or in other manner) decreased from a top surface 903a of the guide member 903 toward a bottom surface 903b (not shown in FIGS. 10A-10E) of the guide member 903.

Figure 10B:
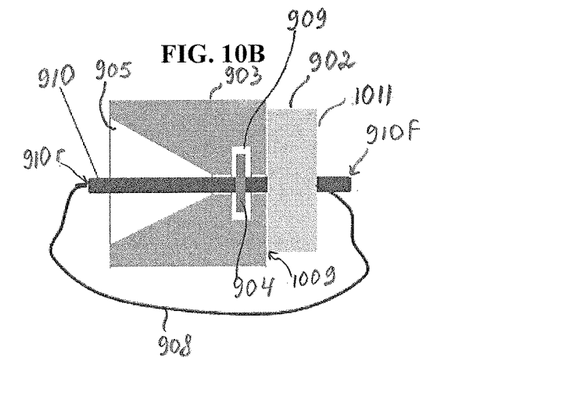
Figure 10C:
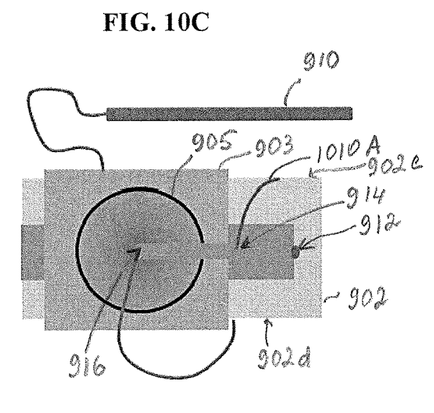
Figure 10D:
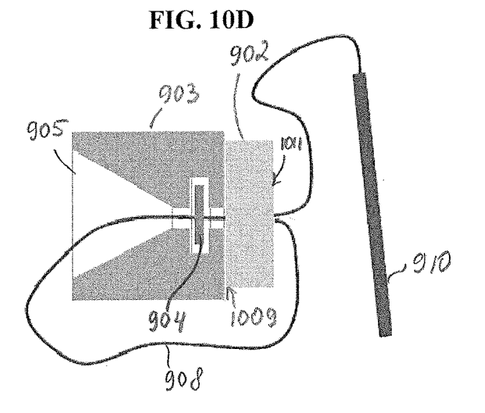

As shown in FIGS. 10A-10D, the guide member 903 is used to guide the needle 910 with the attached suture tail 908 into the third entry point 916. FIG. 10A shows a rear end 910r of the needle 910 in the center of the opening 905. As shown in FIG. 10B, which illustrates a side view of the tissue repair construct of FIG. 10A, the needle 910 is passed through a top, widest portion of the opening 905 at the top surface 903a and guided to advance through the reinforcement material 904 extending through the receiving portion or opening 909 in the guide member 903 and through the first surface 1009 of the graft 902 at the third entry point 916. In this way, as illustrated in FIG. 10B, a forward end 910f of the needle 910 protrudes from the second surface 1011 of the graft 902. FIGS. 10C and 10D illustrate the needle 910 with the attached suture tail 908 after the needle 910 is passed through the reinforcement material 904 and through the graft 902 at the third entry point 916 and exited at the second surface 1011 of the graft 902.

In the embodiment illustrated, the needle and the attached at least one suture tail are passed around opposed side surfaces 902d, 902e of the graft 902 in a sequential and alternating manner. Thus, a first loop 1010A is formed around the side surface 902e, and a second loop 1010B, shown as partially formed, is formed around the opposite side surface 902d. One skilled in the art will appreciate that the first loop 1010A can be formed around the side surface 902d and the subsequent loops will alternate accordingly.

Figure 10E:
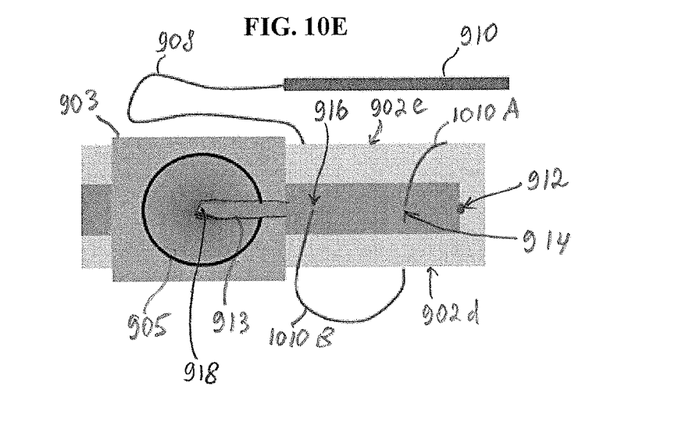

As shown in FIG. 10E, after the needle 910 with the second suture tail 908 is passed through the reinforcement material 904 and through the graft 902 at the third entry point 916 to form the second loop 1010B, the guide member 903 is advanced over the reinforcement material 904 toward the first end 902a of the graft 902 so that the needle 910 with the second suture tail 908 can be guided to pass the reinforcement material 904 and the underlying graft 902 at a subsequent entry point. As discussed above, the guide member 903 can be configured to be advanced over the reinforcement material 904 in any suitable manner. For example, the surgeon can hold the guide member 903 and manually slide it towards the first end 902a of the graft 902. The guide member 903 can include features (e.g., a handle or other similar feature) that can be used to pull the guide member 903 over the reinforcement material 904. Additionally or alternatively, the guide member 903 can include features that can allow temporarily preventing movement of the guide member 903 once it is positioned to aid in aiming the needle.

Because in the illustrated embodiment the loops are formed around the opposed side surfaces 902e, 902d of the graft 902 in the alternating manner, before passing through the reinforcement material 904 and the graft 902 at an entry point 918 subsequent to the entry point 916, the needle 910 is passed around the side surface 902e of the graft. Other loops can be formed in a similar manner, so as to ultimately form a tissue repair construct similar to the construct 600 shown in FIG. 6. However, one skilled in the art will appreciate that suture loops can be created so as to form other patterns, as embodiments are not limited to a specific type of a tissue repair construct.

It should be appreciated that a tissue repair construct can be prepared using any of the guide members (e.g., guide member 803 or 903) described herein or using a guide member having any other suitable configuration.

It should be also appreciated that although illustrated embodiments provide techniques for preparing anterior or posterior cruciate ligaments for ligament reconstruction surgery, the techniques can be adapted for preparation of other ligaments as well.

Having thus described some examples of the described embodiments, various alterations, modifications, and improvements will readily occur to those skilled in the art. Such alterations, modifications, and improvements are intended to be within the spirit and scope of the described embodiments. Accordingly, the foregoing description is by way of example only, and not intended to be limiting.

What is claimed is:

1. A tissue repair construct, comprising:
   a graft material having first and second ends;
   a reinforcement material positioned on a first surface of the graft material adjacent to the first end of the graft material, the reinforcement material having a first end adjacent to the first end of the graft material and a second end remote from the first end of the graft material; and
   a suture integrally formed with the reinforcement material and having first and second suture tails extending from a same end of the reinforcement material and secured to the graft material, the first and second suture tails forming multiple loops along a length of the reinforcement material and the graft material, each loop including a segment of the first and second suture tails extending through the reinforcement material and through the first surface of the graft material at a first position to a second surface of the graft material, around a side portion of the graft material and through the reinforcement material and the first surface of the graft material at a position longitudinally spaced from the first position and exiting the second surface of the graft material,
   wherein at least one of the first and second suture tails freely extends from the first end of the graft material, and wherein the reinforcement material is only formed from a portion of the suture.

2. The tissue repair construct of claim 1, wherein the suture comprises a first suture tail extending from the second end of the reinforcement material and a second suture tail extending from the first end of the reinforcement material.

3. The tissue repair construct of claim 1, further comprising:
   a second reinforcement material positioned on the first surface of the graft material adjacent to the second end of the graft material, the second reinforcement material having a first end adjacent to the second end of the graft material and a second end remote from the second end of the graft material; and
   a second suture secured to the second reinforcement material and the graft material, the second suture forming multiple loops along a length of the second reinforcement material and the graft material, each loop including a segment of the second suture extending through the second reinforcement material and through the first surface of the graft material at a third position to the second surface of the graft material, around a side portion of the graft material and through the second reinforcement material and the first surface of the graft material at a position longitudinally spaced from the third position and exiting the second surface of the graft material,
   the tissue repair construct having at least one loose second suture tail extending from the second end of the graft material.

4. A tissue repair construct, comprising:
   a graft material having first and second ends;
   a monolithic suture coupled to the graft material, the suture comprising a first terminal segment, a second terminal segment, and an intermediate segment disposed between the first terminal segment and the second terminal segment, the intermediate segment including a reinforcement portion that is flattened relative to the first and second terminal segments, the reinforcement portion positioned on a first surface of the graft material adjacent to the first end of the graft material, the reinforcement portion having a first end adjacent to the first end of the graft material and a second end remote from the first end of the graft material, wherein the suture forms multiple loops that surround a length of the reinforcement portion and contact a periphery surface of each of adjacent side portions of the graft material, and wherein the tissue repair construct has at least one loose suture tail extending from the first end of the graft material.

5. The tissue repair construct of claim 4, wherein the reinforcement portion comprises alternating hollow portions and flat portions.

6. The tissue repair construct of claim 4, wherein the second terminal segment is coupled to a needle.

7. The tissue repair construct of claim 4, wherein a portion of the first terminal segment or the second terminal segment is passed through the reinforcement portion and the first surface of the graft material such that the portion extends from a second surface of the graft material, the second surface opposite the first surface.

8. A tissue repair construct, comprising:
a graft material having first and second ends;
a reinforcement material positioned on a first surface of the graft material adjacent to the first end of the graft material, the reinforcement material having a first end adjacent to the first end of the graft material and a second end remote from the first end of the graft material; and
a monolithic suture having a first suture tail extending from the first end of the reinforcement material and a second suture tail extending from the second end of the reinforcement material, the suture secured to the graft material, the first and second suture tails forming multiple loops along a length of the reinforcement material and the graft material, each loop including a segment of the first and second suture tails extending through the reinforcement material and through the first surface of the graft material at a first position to a second surface of the graft material, around a side portion of the graft material such that the segment contacts a periphery surface of the side portion, and through the reinforcement material and the first surface of the graft material at a position longitudinally spaced from the first position and exiting the second surface of the graft material, wherein at least one of the first and second suture tails freely extends from the first end of the graft material, and wherein the reinforcement material is only formed from a portion of the suture.

9. The tissue repair construct of claim 1, wherein a distance between consecutive entry points of the first and second suture tails into the reinforcement material is the same.

10. The tissue repair construct of claim 1, wherein a distance between consecutive entry points of the first and second suture tails into the reinforcement material varies.

11. The tissue repair construct of claim 4, wherein the reinforcement portion has one or more markings to indicate one or more entry points.

12. The tissue repair construct of claim 4, wherein the reinforcement portion comprises a portion of braided, crocheted, knitted, woven, or entangled material.

13. The tissue repair construct of claim 1, wherein the second suture tail is coupled to a needle.

14. The tissue repair construct of claim 1, wherein the width of the reinforcement material is narrower than the width of the graft.

15. The tissue repair construct of claim 1, wherein the reinforcement material extends along a portion of a length of the graft that does not exceed a half-length of the graft.

16. The tissue repair construct of claim 8, wherein a distance between consecutive entry points of the first and second suture tails into the reinforcement material is the same.

17. The tissue repair construct of claim 8, wherein a distance between consecutive entry points of the first and second suture tails into the reinforcement material varies.

* * * * *